US012042329B2

(12) United States Patent
Giphart et al.

(10) Patent No.: US 12,042,329 B2
(45) Date of Patent: Jul. 23, 2024

(54) METHOD AND APPARATUS FOR CONTROLLING AN EYELID DURING IMAGING

(71) Applicant: ArcScan, Inc., Golden, CO (US)

(72) Inventors: Johan E. Giphart, Aurora, CO (US); Andrew K. Levien, Morrison, CO (US); Alexandre M. Nardes, Denver, CO (US); Tom Wilmering, Eldorado Springs, CO (US)

(73) Assignee: ArcScan, Inc., Golden, CO (US)

( * ) Notice: Subject to any disclaimer, the term of this patent is extended or adjusted under 35 U.S.C. 154(b) by 706 days.

(21) Appl. No.: 17/133,233

(22) Filed: Dec. 23, 2020

(65) Prior Publication Data

US 2021/0186458 A1    Jun. 24, 2021

Related U.S. Application Data

(60) Provisional application No. 62/953,093, filed on Dec. 23, 2019.

(51) Int. Cl.
*A61B 8/10* (2006.01)
*A61B 17/02* (2006.01)
*A61B 8/00* (2006.01)
*A61B 17/00* (2006.01)

(52) U.S. Cl.
CPC ............ *A61B 8/10* (2013.01); *A61B 17/0231* (2013.01); *A61B 8/40* (2013.01); *A61B 2017/00951* (2013.01); *A61B 2560/06* (2013.01)

(58) Field of Classification Search
CPC ......... A61B 8/10; A61B 8/40; A61B 17/0231; A61B 2017/00951; A61B 2560/06
USPC ......................................................... 600/236
See application file for complete search history.

(56) References Cited

U.S. PATENT DOCUMENTS

| 4,245,250 | A   |   | 1/1981  | Tiemann           |
|-----------|-----|---|---------|-------------------|
| 4,817,432 | A   |   | 4/1989  | Wallace et al.    |
| 5,029,587 | A   |   | 7/1991  | Baba et al.       |
| 5,183,060 | A   | * | 2/1993  | Shito ........... A61F 13/068 602/56 |
| 5,293,871 | A   |   | 3/1994  | Reinstein et al.  |
| 5,331,962 | A   |   | 7/1994  | Coleman et al.    |
| 6,315,727 | B1  |   | 11/2001 | Coleman et al.    |
| 6,491,637 | B2  |   | 12/2002 | Foster et al.     |

(Continued)

FOREIGN PATENT DOCUMENTS

WO    WO-2007011763 A2 *  1/2007  ............ A61K 47/14

OTHER PUBLICATIONS

Official Action (with English translation) for Chinese Patent Application No. 202023141253.0, dated Feb. 17, 2022 3 pages.

(Continued)

*Primary Examiner* — Eduardo C Robert
*Assistant Examiner* — David C Comstock
(74) *Attorney, Agent, or Firm* — Sheridan Ross P.C.

(57) ABSTRACT

Apparatuses, systems, and methods are provided herein to control movement of a patient's eyelid during a diagnostic procedure such as scanning the patient's eye with an ultrasound or optical imaging device. Strips having a non-adhesive portion and an adhesive portion are attached to each eyelid. The patient can then pull on distal ends of the strip to open the patient's eye and press the strips into an eyepiece to hold the patient's eyelids and keep the patient's eye open.

23 Claims, 10 Drawing Sheets

(56) References Cited

U.S. PATENT DOCUMENTS

| | | | |
|---|---|---|---|
| 6,675,805 B1* | 1/2004 | Graether | A61B 46/00 128/849 |
| 6,887,203 B2 | 5/2005 | Phillips et al. | |
| 7,048,690 B2 | 5/2006 | Coleman et al. | |
| 8,317,702 B2 | 11/2012 | Yu et al. | |
| 8,317,709 B2 | 11/2012 | Eilers et al. | |
| 8,496,588 B2 | 7/2013 | Eilers et al. | |
| 8,510,883 B2 | 8/2013 | Eilers et al. | |
| 8,517,936 B1* | 8/2013 | Townsend | A61B 17/0231 600/236 |
| 8,739,804 B2* | 6/2014 | Cohen | A45D 40/30 132/200 |
| 8,758,252 B2 | 6/2014 | Eilers et al. | |
| 9,039,623 B2 | 5/2015 | Eilers et al. | |
| 9,149,254 B2 | 10/2015 | Watson | |
| 9,597,059 B2 | 3/2017 | Watson et al. | |
| 2005/0115569 A1* | 6/2005 | Davis | A61B 17/0231 128/849 |
| 2005/0159775 A1* | 7/2005 | Reynolds | A61B 17/0231 606/205 |
| 2009/0192389 A1* | 7/2009 | Eilers | A61B 3/1005 600/459 |
| 2013/0237826 A1 | 9/2013 | Levien | |
| 2014/0009741 A1 | 1/2014 | Levien et al. | |
| 2014/0049752 A1 | 2/2014 | Ellers et al. | |
| 2014/0249422 A1 | 9/2014 | Ellers et al. | |
| 2015/0238166 A1 | 8/2015 | Heath et al. | |
| 2016/0166235 A1 | 6/2016 | Levien et al. | |
| 2016/0270762 A1 | 9/2016 | Watson et al. | |
| 2017/0119345 A1 | 5/2017 | Levien et al. | |
| 2018/0243039 A1* | 8/2018 | Ramires | A61B 46/00 |
| 2019/0133582 A1* | 5/2019 | Eaves | A61B 17/085 |
| 2019/0274413 A1* | 9/2019 | Nojiri | C09J 7/20 |
| 2019/0290939 A1 | 9/2019 | Watson et al. | |
| 2020/0015789 A1 | 1/2020 | Johnson | |
| 2021/0204906 A1 | 7/2021 | Giphart et al. | |
| 2021/0353252 A1 | 11/2021 | Reinstein et al. | |

OTHER PUBLICATIONS

U.S. Appl. No. 17/359,128, filed Jun. 25, 2021, Giphart et al.
U.S. Appl. No. 17/411,570, filed Aug. 25, 2021, Giphart et al.
Atchison et al., "Optics of the Human Eye", Butterworth-Heinemann, 1st Edliton, Feb. 29, 2000, ISBN 9780750637756, 288 pages, abstract only, 3 pages.
Coleman, et al., "Ultrasonography of the Eye and Orbit", Lippincott Williams & Wilkins, Second Edition, 2006, 205 pages, uploaded in 3 parts.
Official Action (with English translation) for Chinese Patent Application No. 202023141253.0, dated Oct. 27, 2021 6 pages.
Notice of Allowance with machine translation for Chinese Patent Application No. 202023141253.0, dated May 13, 2022 3 pages.
"Melinex 329," Datasheet, retrieved from https://usa.dupontteijinfilms.com/wp-content/uploads/2017/01/329-Datasheet.pdf, DuPont Teijin Films, Mar. 16, 2016, 2 pages.
Pavlin et al., "Ultrasound Biomicroscopy in Plateau Iris Syndrome," American Journal of Ophthalmology, Apr. 1992, vol. 113(4), pp. 390-395, abstract only, 1 page.

* cited by examiner

METHOD AND APPARATUS FOR CONTROLLING AN EYELID DURING IMAGING

CROSS-REFERENCE TO RELATED APPLICATIONS

This application claims the benefits, under 35 U.S.C. § 119(e), of U.S. Provisional Application Ser. No. 62/953,093 entitled "A Method and Apparatus for Controlling an Eyelid During Imaging" filed Dec. 23, 2019 which is incorporated herein by reference.

FIELD OF INVENTION

The present invention relates to a method for holding an eyelid open and preventing involuntary blinking during an imaging procedure while ensuring patient safety and comfort as well as providing the ability to adjust the amount of tension on the eyelid as needed.

BACKGROUND OF THE INVENTION

Ultrasonic imaging has found use in accurate and reproducible measurements of structures of the eye, such as, for example, the cornea and lens capsule. Such measurements provide an ophthalmic surgeon valuable information that can be used to guide various surgical procedures for correcting refractive errors such as LASIK and lens replacement. They also provide diagnostic information after surgery has been performed to assess the geometrical location of corneal features such as the LASIK scar and lens features such as lens connection, position and orientation. This allows the surgeon to assess post-surgical changes in the cornea or lens and to take steps to correct any problems that develop.

Except for on-axis measurements, dimensions and locations of eye components behind the iris cannot be fully determined by optical means. Ultrasonic imaging in the frequency range of about 5 MHz to about 80 MHz can be applied to make accurate and precise measurements of structures of the eye, such as the cornea, lens capsule, ciliary muscle and the like.

An ultrasound scanning apparatus is described in the following issued US patents, all of which are incorporated herein by reference:
1. U.S. Pat. No. 7,048,690 "Precision Ultrasound Measurement for Intraocular Lens Placement"
2. U.S. Pat. No. 8,758,252 "Innovative Components for an Ultrasonic Arc Scanning Apparatus"
3. U.S. Pat. No. 8,496,588 "Procedures for an Ultrasonic Arc Scanning Apparatus"
4. U.S. Pat. No. 8,317,709 "Alignment and Imaging of an Eye with an Ultrasonic Scanner"
5. U.S. Pat. No. 9,149,254 "Alignment and Imaging of an Eye with an Ultrasonic Scanner"
6. U.S. Pat. No. 9,597,059 "Tracking Unintended Eye Movements in an Ultrasonic Scan of the Eye"

At a center frequency of about 38 MHz, a typical arc scanner has an axial resolution of about 20 microns and a lateral resolution of about 150 microns. The reproducibility of an arc scanner is typically about 2 microns.

The ultrasonic system described herein is capable of accurately moving an ultrasound transducer with respect to a known reference point on a patient's head. Further improvements allow for tracking of unintended eye motions during scanning as disclosed in U.S. patent application Ser. No. 13/894,741 which is incorporated herein by reference.

Ultrasonic imaging has been used in corneal procedures such as LASIK to make accurate and precise images and maps of cornea thickness which include epithelial thickness, Bowman's layer thickness and images of LASIK flaps. At a center frequency of about 38 MHz, a typical arc scanner image has an axial resolution of about 20 microns and a lateral resolution of about 150 microns. The operator and instrument reproducibility of an arc scanner image is typically about 2 microns.

New procedures such as implantation of accommodative lenses may provide nearly perfect vision without spectacles or contact lenses. Implantation of accommodative lenses requires precision measurements of, for example, the position and width of the natural lens for successful lens powering and implantation. Ultrasonic imaging can be used to provide the required accurate images of the natural lens especially where the zonules attach the lens to the ciliary body which is well off-axis and behind the iris and therefore not accessible to optical imaging.

Recent advances in ultrasonic imaging have allowed images of substantially the entire lens capsule to be made. This has opened up the ability of diagnostic devices to assist in both research of lens implantation devices and strategies, and to planning, executing and follow-up diagnostics for corrective lens surgery including specialty procedures such as glaucoma and cataract treatments as well as implantation of clear intraocular lenses including accommodative lens.

A phakic intraocular lens (PIOL) is a special kind of intraocular lens that is implanted surgically into the eye to correct myopia. It is called "phakic" (meaning "having a lens") because the eye's natural lens is left untouched. Intraocular lenses that are implanted into eyes after the eye's natural lens has been removed during cataract surgery are known as pseudophakic. Phakic intraocular lenses are considered for patients with high refractive errors when laser options, such as LASIK and PRK are not the best surgical options.

Ultrasound provides key measurements behind iris not before available and can reduce explant rates by about ten times.

Other new procedures such as implantation of stents in or near the suprachoroid may provide part or all of a treatment for glaucoma. Ultrasonic imaging can be used to provide the required accurate images in the corner of the eye between the sclera and the iris (in the region of the suprachoroidal space to the scleral spur) which is well off-axis and essentially inaccessible to optical imaging.

The speed of transducer motion in a precision scanning device such as described, for example, in U.S. Pat. No. 8,317,709, is limited because its movement is in a bath of water and excessive speed of motion of the transducer and its carriage can result in vibration of the entire instrument. In practice, a set of ultrasound scans can be carried out in about 1 to about 3 minutes from the time the patient's eye is immersed in water to the time the water is drained from the eyepiece. The actual scanning process itself can be carried out in several tens of seconds, after the operator or automated software completes the process of centering and range finding. As is often the case, the patient may move his or her head slightly or may move his or her eye in its socket during this time. In some cases, the patient's heart beat can be detected as a slight blurring of the images. If patient movements are large, the scan set can always be repeated.

Imaging of the internal anatomy of the eye requires some form of energy to enter the eye and be reflected back to a transducer for detection. Ultrasound is one such type of energy, as is light. A common challenge during these procedures is to keep the eyelids from blocking the incoming or returning energy either due to the natural position of the eyelids or during blinking by the patient. The present disclosure provides a means for preventing an eyelid from closing and/or to retract an eyelid further beyond its natural location to increase the range and space available for the imaging system.

Eyelids can be taped up to the forehead or down to the cheek with common medical tape. However, this doesn't provide the instrument operator with the ability to adjust or control the amount of eyelid opening very well, nor to relax the eyelids, for instance between scanning, and then reapply the tension.

An eye speculum, installed under a patient's eyelid, can also be used for the described purpose; however, an eye speculum doesn't allow for control by the patient or instrument operator either. An eye speculum is often quite uncomfortable for some patients.

There remains, therefore, a need for a method and apparatus that can be used to hold an eyelid open and prevent involuntary blinking during an imaging procedure while ensuring patient safety and comfort as well as provide the ability to adjust the amount of tension on the eyelid as needed.

SUMMARY OF THE INVENTION

These and other needs are addressed by the present disclosure. The various embodiments and configurations of the present disclosure are directed generally to ultrasonic imaging of biological materials such as the cornea, sclera, iris and lens in the anterior segment of an eye and in particular directed to a method for holding an eyelid open and preventing involuntary blinking during an eye imaging procedure.

The present disclosure comprises a narrow strip of adhesive that can be applied to the eyelid combined with a strip that extends the tape in a non-adhesive manner to allow a person to pull on the extension in order to pull on the eyelid. The adhesive strip is approximately the size of the eyelid or smaller so as to only pull on the eyelid directly and minimize the amount of adhesive connecting with the surrounding tissue. When not in use, the adhesive strip can be protected by a liner or tab for ease of handling prior to use and/or to protect the adhesive from degradation prior to use.

The eyelid retractor strip can be manufactured in several ways, including but not limited to applying double-sided adhesive tape to a non-adhesive strip, or single-sided adhesive tape applied to a non-adhesive strip with the adhesive side overhanging the non-adhesive strip, or applying adhesive locally on a non-adhesive strip. The non-adhesive material can be either elastic or stiffer such as for example polyester film sold under the trademark MELINEX®.

As discussed below, these eye strips can be used for ultrasound imaging using an arc scanning device and its disposable eye piece.

These eye strips can also be used for other imaging field of view devices such as OCT instruments, topography devices such the OCULUS Pentacam, and measurement devices such as tonometers and the like. These eye strips can also be used for eye treatments such as applying various drops.

One specific embodiment of the present disclosure is an apparatus for controlling eyelid movement, comprising a base strip extending between a first end and a second end of the base strip by a first length; and an adhesive strip extending between a first end and a second end of the adhesive strip by a second length, wherein at least one surface of the adhesive strip has is an adhesion surface that is positioned on a surface of the base strip, and wherein a portion of the adhesive strip overhangs one of the first end or the second end of the base strip by a third distance that is between approximately 6.5% and 13.5% of the second distance.

In some embodiments, the base strip has a lower Young's modulus than the adhesive strip. In various embodiments, the base strip is made from polyester film sold under the trademark MELINEX®. In some embodiments, the second distance is between approximately 35% and 40% of the first distance. In various embodiments, both surfaces of the adhesive strip are adhesion surfaces, and a liner is positioned on the adhesion surface oriented away from the base strip.

In some embodiments, the base strip is a polyester film with a thickness between surfaces of between approximately 23 microns to 350 microns. In various embodiments, the adhesion surface of the adhesive strip comprises a pressure sensitive tackified acrylate adhesive. In some embodiments, the adhesive strip comprises a backing that is a transparent, perforated ethylene vinyl acetate. In various embodiments, the base strip and the adhesive strip are each approximately 0.75 inches wide.

Another particular embodiment of the present disclosure is a system for controlling eyelid movement, comprising an eye diagnostic device having an eye piece with a top edge and a bottom edge, wherein the eye piece is configured to receive a patient's eye in a space between the top edge and the bottom edge; a first eye strip having a first adhesive strip joined to a first base strip, wherein the first adhesive strip is shorter than the first base strip, wherein a portion of the first adhesive strip overhangs an end of the first base strip, wherein the overhanging portion of the first adhesive strip is configured to adhere to an upper eyelid of the patient's eye, and wherein the first eye strip presses into the top edge of the eyepiece with a first friction force to resist an eyelid closing force; and a second eye strip having a second adhesive strip joined to a second base strip, wherein the second adhesive strip is shorter than the second base strip, wherein a portion of the second adhesive strip overhangs an end of the second base strip, wherein the overhanging portion of the second adhesive strip is configured to adhere to a lower eyelid of the patient's eye, and wherein the second eye strip presses into the bottom edge of the eyepiece with a second friction force to resist the eyelid closing force.

In some embodiments, the first adhesive strip comprises an adhesion surface and an opposing non-adhesion surface, wherein the non-adhesion surface contacts the top edge of the eyepiece to produce the first friction force. In various embodiments, the top edge and the bottom edge of the eyepiece are part of a rubber face seal that is joined to a rigid portion of the eyepiece. In some embodiments, the rubber face seal is a silicone thermo-plastic elastomer. In various embodiments, the overhanging portion of the first adhesive strip is between approximately 6.5% and 13.5% of an overall length of the first adhesive strip. In some embodiments, the overall length of the first adhesive strip is between approximately 35% and 40% of an overall length of the first base strip. In various embodiments, the adhesion surface of the first adhesive strip comprises a pressure sensitive tackified acrylate adhesive.

A further embodiment of the present disclosure is a method for controlling eyelid movement, comprising providing a first eye strip having a first adhesive strip joined to a first base strip, wherein the first adhesive strip is shorter than the first base strip, and wherein a portion of the first adhesive strip overhangs an end of the first base strip; adhering the overhanging portion of the first adhesive strip to an upper eyelid of a patient; providing a second eye strip having a second adhesive strip joined to a second base strip, wherein the second adhesive strip is shorter than the second base strip, and wherein a portion of the second adhesive strip overhangs an end of the second base strip; adhering the overhanging portion of the second adhesive strip to a lower eyelid of the patient; and pressing the patient's face into an eyepiece of an eye diagnostic device such that a first friction force is created between the first eye strip and a top edge of the eyepiece and a second friction force is created between the second eye strip and a bottom edge of the eyepiece, wherein the first and second friction forces resist a closing force of the upper and lower eyelids of the patient.

In some embodiments, the method further comprises forming a watertight seal between the face of the patient with the first and second eye strips adhered to the upper and lower eyelids of the patient and the eyepiece. In various embodiments, the method further comprises filling a space defined by the eyepiece with a fluid, wherein the eye diagnostic device in an ultrasound imaging device configured to transmit an ultrasound pulse through the fluid and into the eye of the patient. In some embodiments, the method further comprises filling a space defined by the eyepiece with a fluid, wherein the eye diagnostic device in an optical imaging device configured to transmit an optical pulse through the fluid and into the eye of the patient. In various embodiments, the method further comprises pulling a distal end of the first base strip to impose a force on the first eye strip that is at least greater than the first friction force to further open the eye of the patient. In some embodiments, the overhanging portion of the first adhesive strip is between approximately 6.5% and 13.5% of an overall length of the first adhesive strip. In various embodiments, the overall length of the first adhesive strip is between approximately 35% and 40% of an overall length of the first base strip.

The following definitions are used herein:

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The phrases at least one, one or more, and and/or are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

Anterior means situated at the front part of a structure; anterior is the opposite of posterior.

An A-scan is a representation of a rectified, filtered reflected acoustic signal as a function of time, received by an ultrasonic transducer from acoustic pulses originally emitted by the ultrasonic transducer from a known fixed position relative to an eye component.

An accommodative lens, also known as a presbyopic lens or presby lens, is an artificial intraocular lens that changes its focal distance in response to contraction of the ciliary body. When successfully implanted, an accommodative lens reverses presbyopia, the inability of the eye to change its focal distance from far to near.

Accuracy as used herein means substantially free from measurement error.

Aligning means positioning the acoustic transducer accurately and reproducibly in all three dimensions of space with respect to a feature of the eye component of interest (such as the center of the pupil, center of curvature or boundary of the cornea, lens, retina, etcetera).

The anterior chamber comprises the region of the eye from the cornea to the iris.

The anterior segment comprises the region of the eye from the cornea to the back of the lens.

Automatic refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Auto-centering means automatically, typically under computer control, causing centration of the arc scanning transducer with the eye component of interest.

A B-scan is a processed representation of A-scan data by either or both of converting it from a time to a distance using acoustic velocities and by using grayscales, which correspond to A-scan amplitudes, to highlight the features along the A-scan time history trace (the latter also referred to as an A-scan vector).

Centration means substantially aligning the center of curvature of the arc scanning transducer in all three dimensions of space with the center of curvature of the eye component of interest (such as the cornea, pupil, lens, retina, etcetera) such that rays from the transducer pass through both centers of curvature. A special case is when both centers of curvature are coincident.

An eye speculum is an instrument or device for keeping the eyelids apart during an inspection of or a procedure on or an operation on the eye. Examples are made from plated steel wire or plastic. Luer's, Von Graefe's, and Steven's are the most common types.

Fiducial means a reference, marker or datum in the field of view of an imaging device.

Fixation means having the patient focus an eye on an optical target such that the eye's optical axis is in a known spatial relationship with the optical target. In fixation, the light source is axially aligned in the arc plane with the light source in the center of the arc so as to obtain maximum signal strength such that moving away from the center of the arc in either direction results in signal strength diminishing equally in either direction away from the center.

A guide or guide track e is an apparatus for directing the motion of another apparatus.

An imaging ultrasound transducer is the device that is responsible for creating the outgoing ultrasound pulse and detecting the reflected ultrasound signal that is used for creating the A-Scans and B-Scans.

An intraocular lens is an artificial lens that is implanted in the eye to take the place of the natural lens.

LASIK is a procedure performed on the cornea for correcting refractive errors, such as myopia, hyperopia, and astigmatism. Commonly, an excimer laser selectively removes tissue from the inside of the cornea, after it is exposed, by cutting a thin flap, so as to reshape the external shape of the cornea.

The natural lens (also known as the aquula or crystalline lens) is a transparent, biconvex structure in the eye that, along with the cornea, helps to refract light to be focused on the retina. The lens, by changing shape, functions to change the focal distance of the eye so that it can focus on objects at various distances, thus allowing a sharp real image of the object of interest to be formed on the retina. This adjustment of the lens is known as accommodation. The lens is located in the anterior segment of the eye behind the iris. The lens is suspended in place by the zonular fibers, which attach to the lens near its equatorial line and connect the lens to the ciliary body. The lens has an ellipsoid, biconvex shape whose size and shape can change due to accommodation and due to growth during aging. The lens is comprised of three main parts: namely the lens capsule, the lens epithelium, and the lens fibers. The lens capsule forms the outermost layer of the lens and the lens fibers form the bulk of the interior of the lens. The cells of the lens epithelium, located between the lens capsule and the outermost layer of lens fibers, are generally found only on the anterior side of the lens.

Ophthalmology means the branch of medicine that deals with the eye.

Optical as used herein refers to processes that use light rays.

Phakic intraocular lenses, or phakic lenses, are lenses made of plastic or silicone that are implanted into the eye permanently to reduce a person's need for glasses or contact lenses. Phakic refers to the fact that the lens is implanted into the eye without removing the eye's natural lens. During phakic lens implantation surgery, a small incision is normally made in the front of the eye. The phakic lens is inserted through the incision and placed just in front of or just behind the iris.

Positioner means the mechanism that positions a scan head relative to a selected part of an eye. In the present disclosure, the positioner can move back and forth along the x, y or z axes and rotate in the β direction about the z-axis. Normally the positioner does not move during a scan, only the scan head moves. In certain operations, such as measuring the thickness of a region, the positioner may move during a scan.

Precise as used herein means sharply defined and repeatable.

Precision means how close in value successive measurements fall when attempting to repeat the same measurement between two detectable features in the image field. In a normal distribution precision is characterized by the standard deviation of the set of repeated measurements. Precision is very similar to the definition of repeatability.

Presbyiopia is typically caused by a loss of elasticity of the natural lens inside the eye. This occurs as part of the ageing process and, although it cannot be 'cured', it can be corrected by wearing glasses or implanting an artificial lens.

The pulse transit time across a region of the eye is the time it takes a sound pulse to traverse the region.

Refractive means anything pertaining to the focusing of light rays by the various components of the eye, principally the cornea and lens.

Registration as used herein means aligning.

Saccades are quick, simultaneous rotations of both eyes in the same direction involving a succession of discontinuous individual rotations of the eye orbit in the eye socket. These rapid motions can be on the order of 20 degrees of rotation with a maximum velocity of 200 degrees/sec and are a part of normal eyesight.

Scan head means the mechanism that comprises the ultrasound transducer, the transducer holder and carriage as well as any guide tracks that allow the transducer to be moved relative to the positioner. Guide tracks may be linear, arcuate or any other appropriate geometry. The guide tracks may be rigid or flexible. Normally, only the scan head is moved during a scan.

Sector scanner is an ultrasonic scanner that sweeps a sector like a radar. The swept area is pie-shaped with its central point typically located near the face of the ultrasound transducer.

A track or guide track is an apparatus along which another apparatus moves. In an ultrasound scanner or combined ultrasound and optical scanner, a guide track is an apparatus along which one or more ultrasound transducers and/or optical probes moves during a scan.

Ultrasonic means sound that is above the human ear's upper frequency limit. When used for imaging an object like the eye, the sound passes through a liquid medium, and its frequency is many orders of magnitude greater than can be detected by the human ear. For high-resolution acoustic imaging in the eye, the frequency is typically in the approximate range of about 5 to about 80 MHz.

An ultrasonic scanner is an ultrasound scanning device utilizing a transducer that both sends and receives pulses as it moves along 1) an arcuate guide track, which guide track has a center of curvature whose position can be moved to scan different curved surfaces; 2) a linear guide track; and 3) a combination of linear and arcuate guide tracks which can create a range of centers of curvature whose position can be moved to scan different curved surfaces.

A vector refers to a single acoustic pulse and its multiple reflections from various eye components. An A-scan is a representation of this data whose amplitude is typically rectified.

The visual axis of the eye is the line joining the object of interest and the fovea and which passes through the nodal points of the eye.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein. By way of example, the phrase from about 2 to about 4 includes the whole number and/or integer ranges from about 2 to about 3, from about 3 to about 4 and each possible range based on real (e.g., irrational and/or rational) numbers, such as from about 2.1 to about 4.9, from about 2.1 to about 3.4, and so on.

The preceding is a simplified summary of the disclosure to provide an understanding of some aspects of the disclosure. This summary is neither an extensive nor exhaustive overview of the disclosure and its various embodiments. It is intended neither to identify key or critical elements of the disclosure nor to delineate the scope of the disclosure but to present selected concepts of the disclosure in a simplified form as an introduction to the more detailed description presented below. As will be appreciated, other embodiments of the disclosure are possible utilizing, alone or in combination, one or more of the features set forth above or described in detail below.

BRIEF DESCRIPTION OF THE DRAWINGS

The present disclosure may take form in various components and arrangements of components, and in various steps and arrangements of steps. The drawings are only for purposes of illustrating the preferred embodiments and are not to be construed as limiting the invention. In the drawings, like reference numerals may refer to like or analogous components throughout the several views.

DETAILED DESCRIPTION OF THE DRAWINGS

The present disclosure comprises a narrow strip of adhesive that can be applied to the eyelid combined with a strip that extends the tape in a non-adhesive manner to allow a person to pull on the extension in order to pull on the eyelid. The adhesive strip is approximately the width and height of the eyelid or smaller so as to only pull on the eyelid directly and minimize the amount of adhesive connecting with the surrounding tissue. When not in use, the adhesive strip can be protected by a liner or tab for ease of handling prior to use and/or to protect the adhesive from degradation prior to use.

The eyelid retractor strip can be manufactured in several ways, including but not limited to applying double-sided adhesive tape to a non-adhesive strip, or single-sided adhesive tape applied to a non-adhesive strip with the adhesive side overhanging the non-adhesive strip, or applying adhesive locally on a non-adhesive strip. The non-adhesive material can be either elastic (for perhaps enhanced tactile feedback) or stiffer (for perhaps ease of manufacturing; e.g., handling and cutting).

Figure 1:
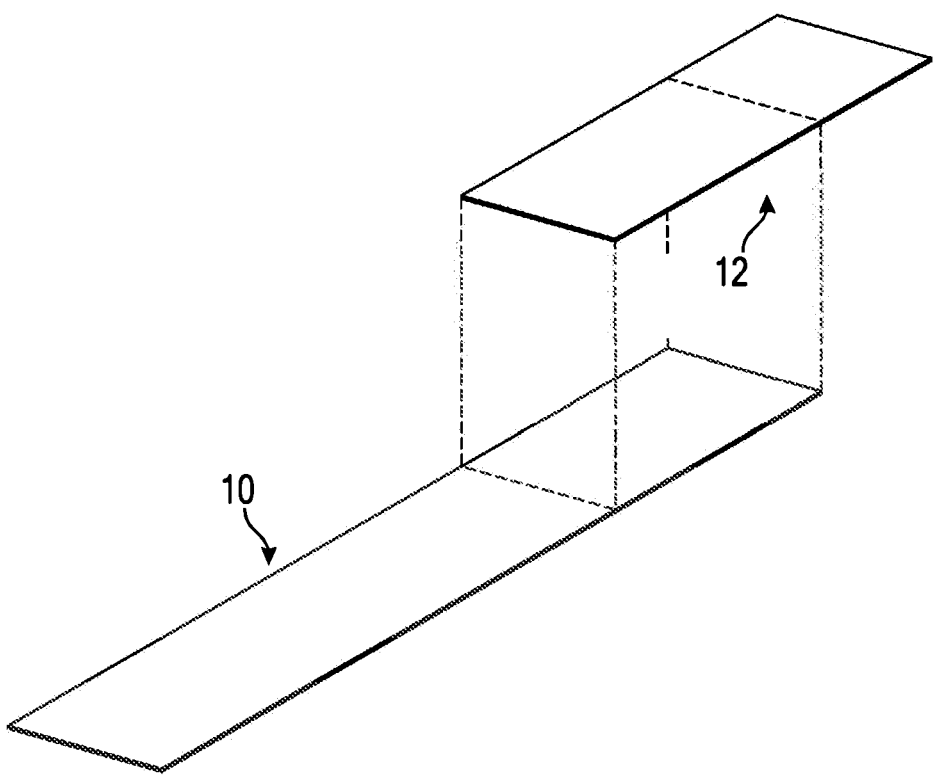
FIG. 1 is a drawing of an eye strip of the present disclosure.

FIG. 1 is a drawing of an eye strip of the present disclosure. The eye strip is approximately 8- to 9-inches long by about ¾-inches wide. The about 8-inch long base strip 10 can be made from an elastic material. Alternatively, it can be made from a stiff material such as, for example, polyester film sold under the trademark MELINEX® 329 polyester film manufactured by Dupont and Tekra (a division of EIS, Inc.) for example. The polyester film sold under the trademark MELINEX® 329 polyester film comes in thicknesses ranging from 23 microns to 350 microns. A 50 micron (2 mil) film is preferred.

A single sided tape, coated with a pressure sensitive tackified acrylate adhesive on one side 12, is affixed on one end of the base strip. A single sided tape such as 3M™ Medical Tape 1527-LX Transpore™ surgical tape, which is about 40 microns (about 1.5 mils) thick, may be used. When the backing on the single sided tape is peeled off exposing the adhesive, the adhesive side of single sided tape is affixed to the base strip such that about 0.25 to about 0.375 inches of single sided tape extends beyond the base strip. The adhesive side of single sided tape attaches the single sided tape to the base tape and about half of the adhesive side of single sided tape is exposed and can be attached to the patient as described below.

This single sided medical tape on a roll (1527LX) comprises a transparent, perforated ethylene vinyl acetate (EVA) backing, coated with a pressure sensitive tackified acrylate adhesive. The liner is a silicone treated, polyethylene coated, one side only, bleached Kraft paper.

Figure 2:
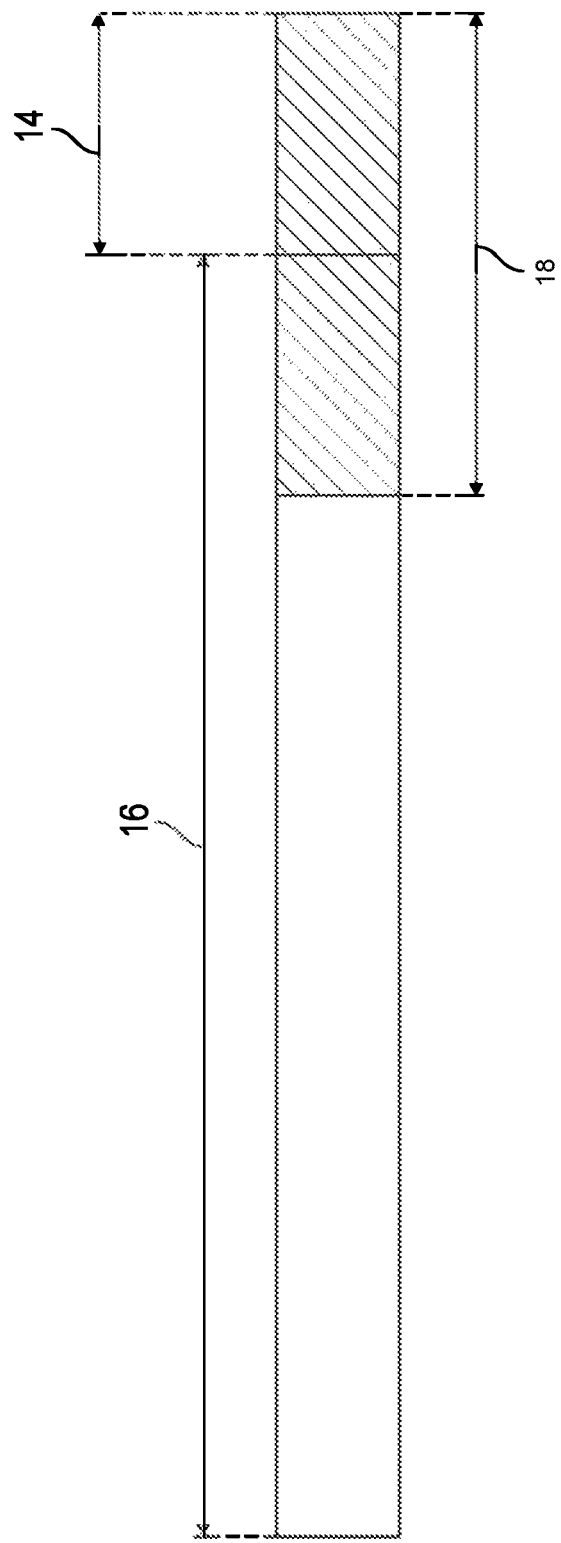
FIG. 2 is another drawing of an eye strip of the present disclosure

FIG. 2 is another drawing of an eye strip of the present disclosure. This figure illustrates the about 8-inches of base strip and the about 3-inches of single sided tape wherein about 2.75 inches of single sided tape is adhered to the base strip and about 0.25 inches of single sided tape extends beyond the single sided tape with its adhesive side facing inward. The dimensions of the base strip and the adhesive strip can be expressed in relative terms that are critical to the function of the eye strip. For example, in some embodiments, the overhanging portion or length 14 of the adhesive strip is between approximately 6.5% and 13.5% of the overall base strip length 16 of the adhesive strip. Thus, the overhanging portion engages the patient's eyelid and the non-overhanging portion binds the adhesive strip to the base strip with a sufficiently strong bond. Moreover, in some embodiments, the overall length of the adhesive strip 18 is between 35% and 40% of the overall length of the base strip. Thus, the strips are sufficiently bonded together, but the base strip is long enough for a patient to grasp and pull a distal end of the base strip.

Figure 3A:
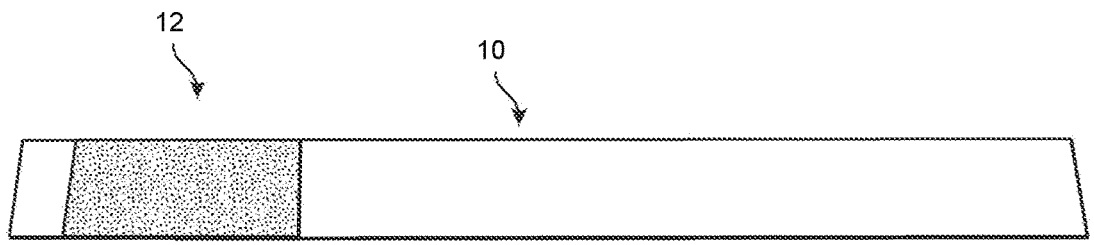
FIGS. 3A and 3b are drawings of an eye strip of the present disclosure.
Figure 3B:
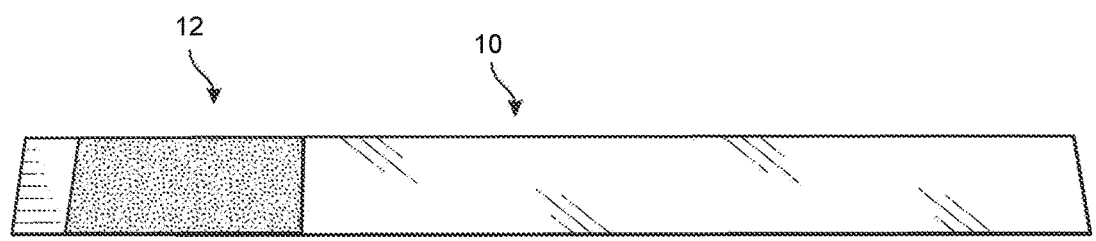

FIGS. 3A and 3B are photos of an eye strip of the present disclosure. The single sided tape is shown on the left side of the base strip extending about a quarter to about three-eighths of an inch beyond the base strip.

Figure 4:
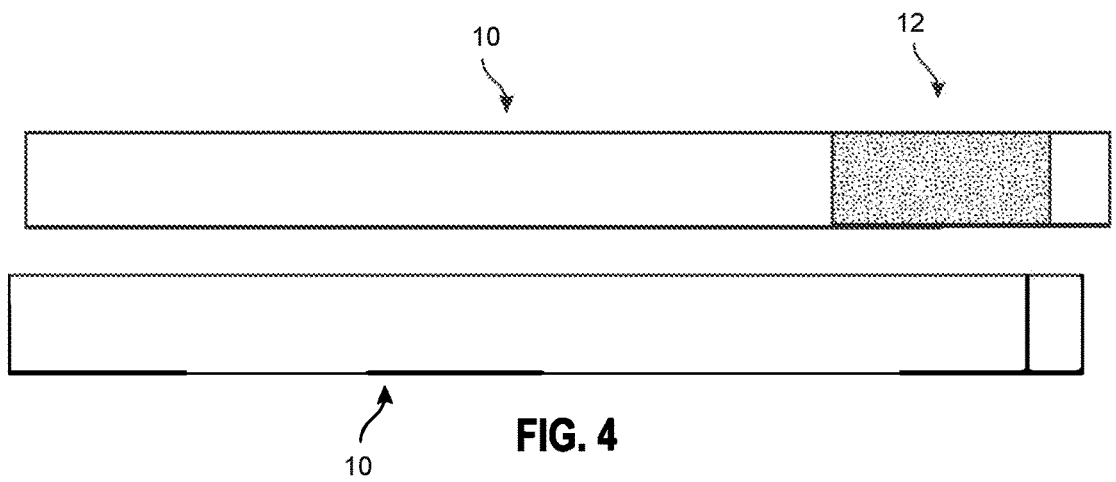
FIG. 4 is another drawing of an eye strip of the present disclosure

FIG. 4 is another photo of eye strips of the present disclosure. This figure shows two different strips with two different base strip materials. The bottom view shows a polyester film sold under the trademark MELINEX® base strip with about a quarter of an inch of the single sided tape extending beyond the base strip. This figure also shows a top view of a low density polyethylene base strip design with the single sided tape visible on the right. This figure shows a bottom view of a polyester film sold under the trademark MELINEX® base strip with about a quarter of an inch of the single sided tape extending beyond the base strip. This figure also shows a top view of a low density polyethylene base strip design with the single sided tape visible on the right.

Figure 5:
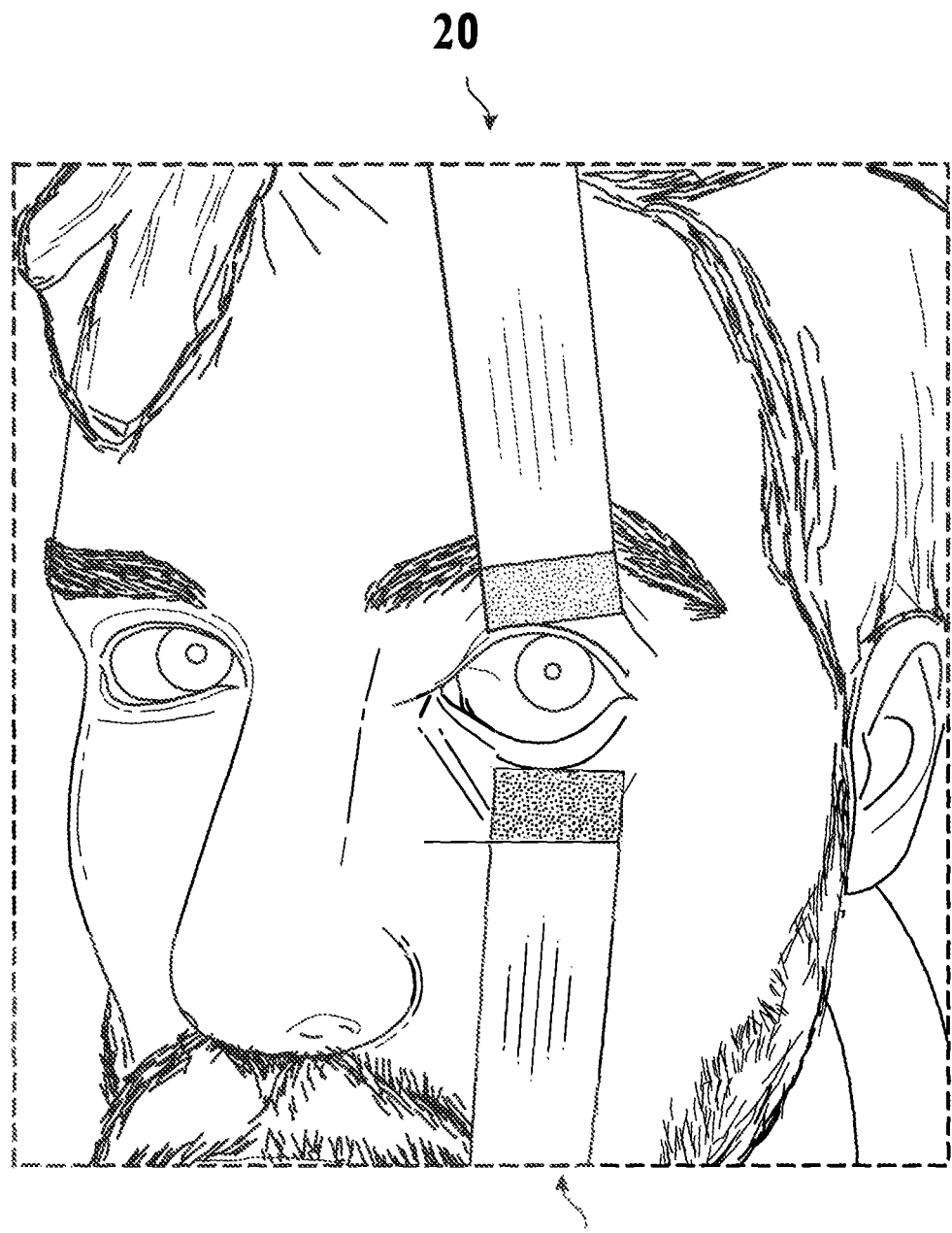
FIG. 5 is a drawing of an eye strip applied to a patient prior to imaging.

FIG. 5 is a photo of an eye strip applied to a patient prior to imaging. One assembled eye strip 20 is attached to the upper eyelid using the short section of exposed adhesive on the one sided tape. A second assembled eye strip 22 is attached to the lower eyelid using the short section of exposed adhesive on its one sided tape. The patient pulls their own eyelid open then positions himself at the scanning machine as described below.

Eyelids can be taped up to the forehead or down to the cheek with common medical tape; however, this doesn't provide the instrument operator with the ability to adjust or control the amount of eyelid opening very well, nor to relax the eyelids, for instance between scanning, and then reapply the tension.

An eye speculum, installed under a patient's eyelid, can also be used for the described purpose; however, an eye speculum doesn't allow for control by either the patient or instrument operator. An eye speculum is often quite uncomfortable for some patients as the majority of the designs reach under the eye-lid with metal wires.

Figure 6:
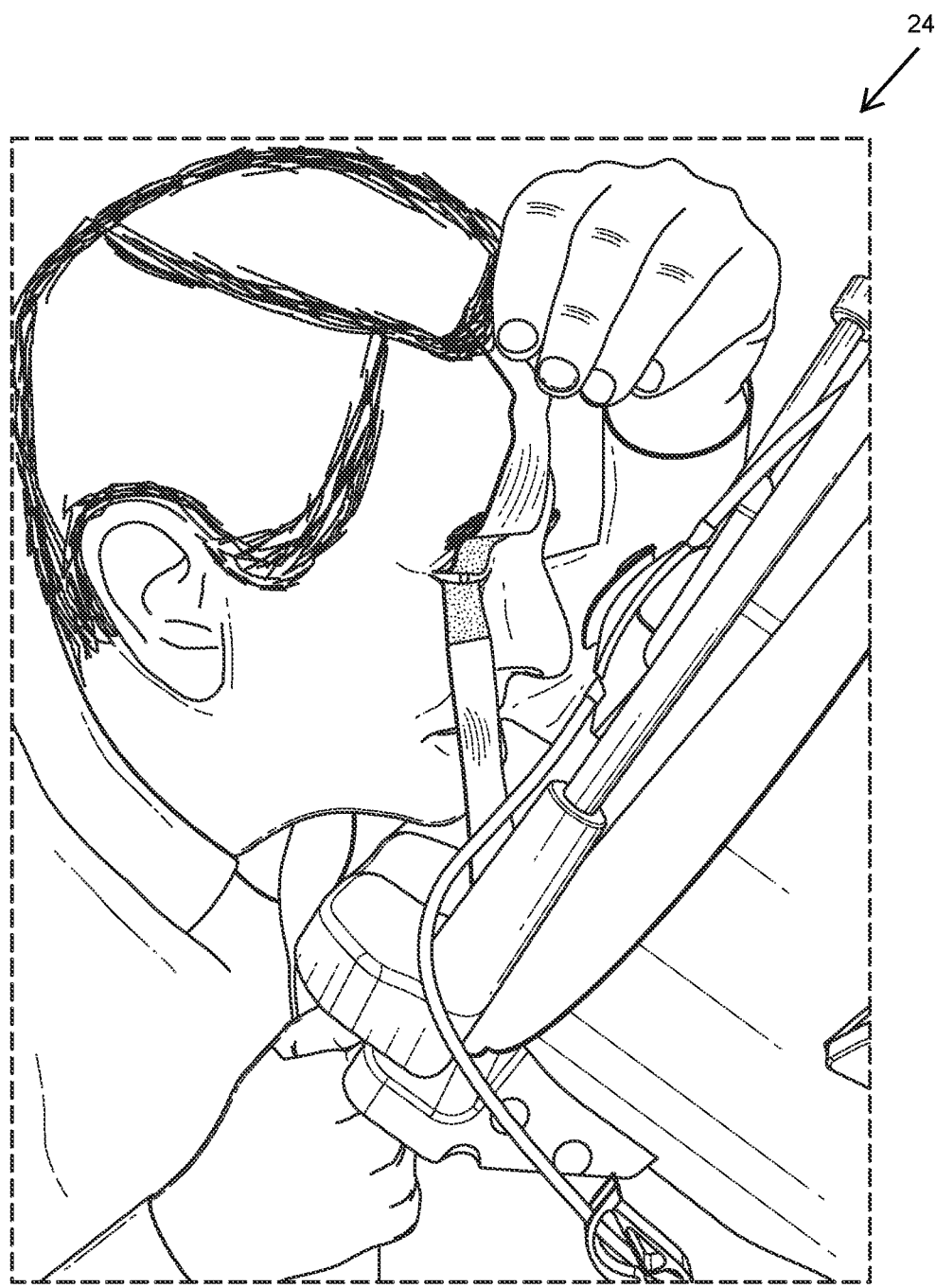
FIG. 6 is a drawing of an eye strip applied to a patient during imaging.

FIG. 6 is a photo 24 of an eye strip attached to a patient during imaging. As in FIG. 5, the patient pulls their own eyelid open and holds their eyelid comfortably open for the duration of the scan session (typically 3 or 4 minutes). When the taped eye engages the eye seal, the soft elastomer is able to seal over the tape when saline solution is introduced into the eye seal cup (see FIG. 8). When the patient is engaged with the eye seal, the patient can further pull on the strips as necessary to maintain the eyelid open, maintain a level of tension on the opened eyelid, maintain a good seal when saline is introduced into the eye seal cup and maintain his comfort during scanning.

With the use of the eye strip of the present disclosure, the patient has a level of control and comfort that cannot be achieved with an eye speculum.

Figure 7:
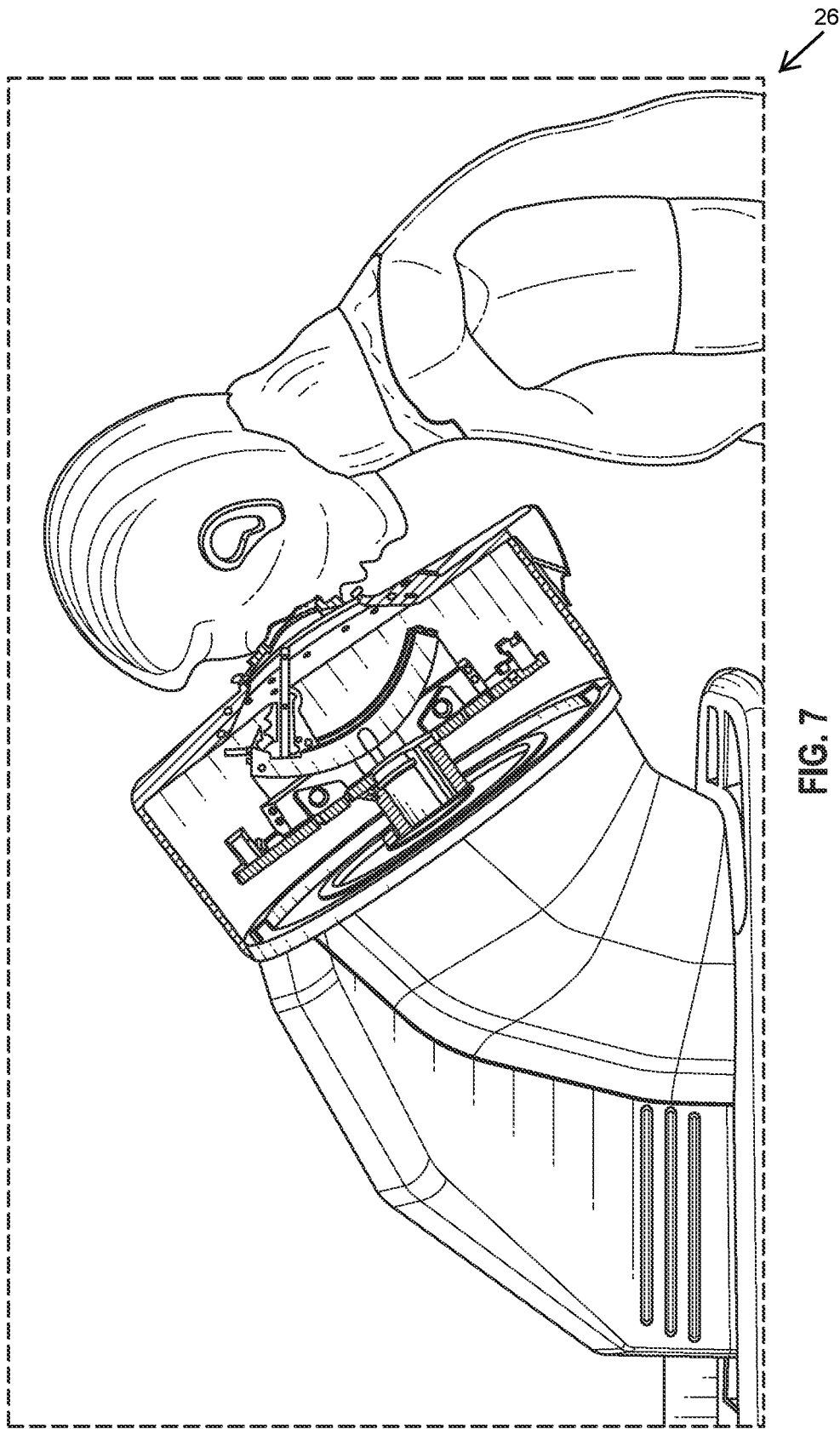
FIG. 7 is a drawing of an ultra sound scanner and patient being imaged.

FIG. 7 is a rendering 26 of an ultrasound scanner and patient being imaged. In this rendering, the bucket or compartment which holds the positioner and scan head assemblies and the water used during scanning, is shown in a cutaway view. This cutaway view also shows the ultrasound transducer with the probe tip very close to one side of the eye seal membrane and with the patient's eye on the other side of the membrane.

Figure 8:
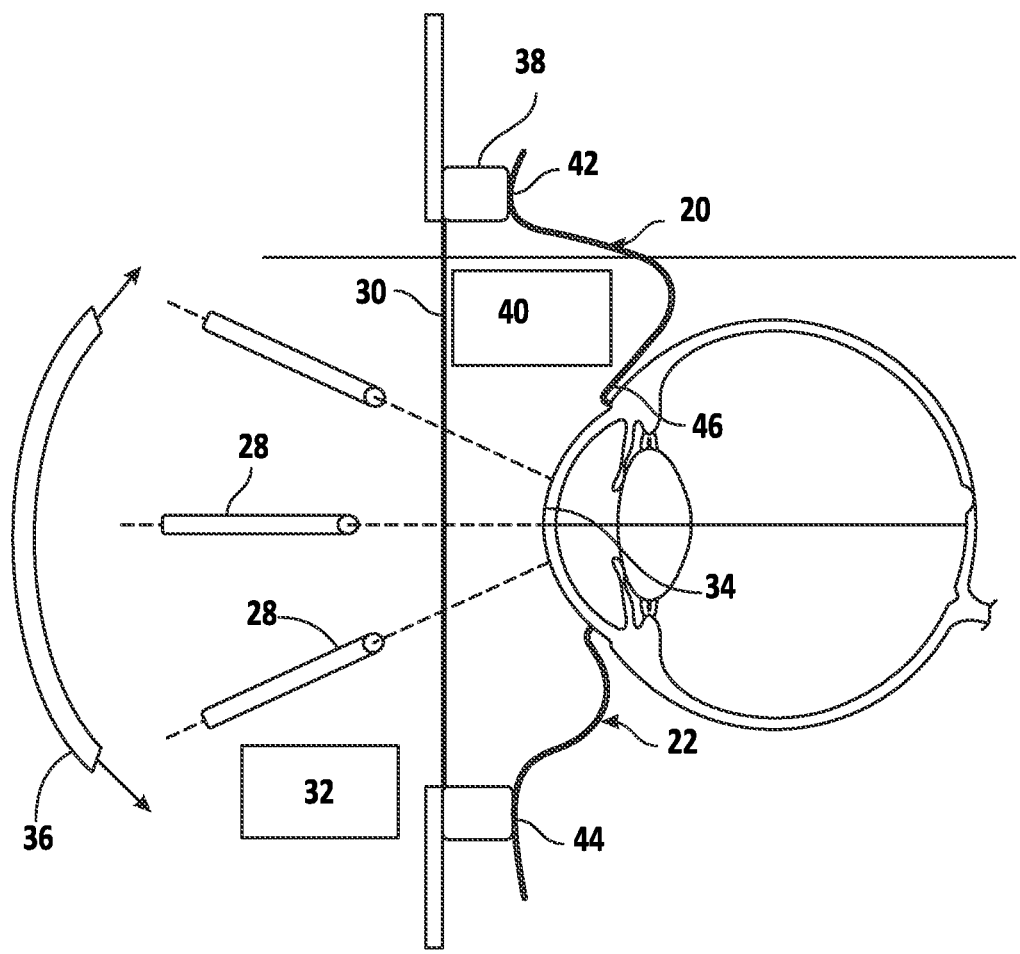
FIG. 8 is a schematic showing the relationship between the ultrasound transducer, the eye seal and the patient's eye.

FIG. 8 is a schematic showing the relationship between the ultrasound transducer, the eye seal and the patient's eye. In this figure, an ultrasound transducer (also known as an ultrasound probe 28) is shown in three consecutive positions as it moves along an arcuate guide track in an arc motion 36. The dot-dash lines represent the ultrasound beam paths. As noted previously, the scan head and probe are immersed in water (scanner fluid 32) and a membrane 30 contained by the eye piece or eye seal 38 separates the scanner fluid from the saline solution in the eye seal cup. The eye seal 38 presses against the eyebrow 42 and the cheek bone 44. The eye strips 20, 22 contact the eyelids 46. The cornea 34 of the eye is immersed in the saline solution 40 and the eye is sealed against a soft material, formed from a silicone thermoplastic elastomer, that is part of the eye piece assembly. Thus the saline solution, the membrane and the scanner fluid form an acoustic path that has substantially the same acoustic impedance as the anterior segment components of the eye. The acoustic path is also optically transparent and allows an optical camera to assist in centering the eye just prior to scanning.

Figure 9:
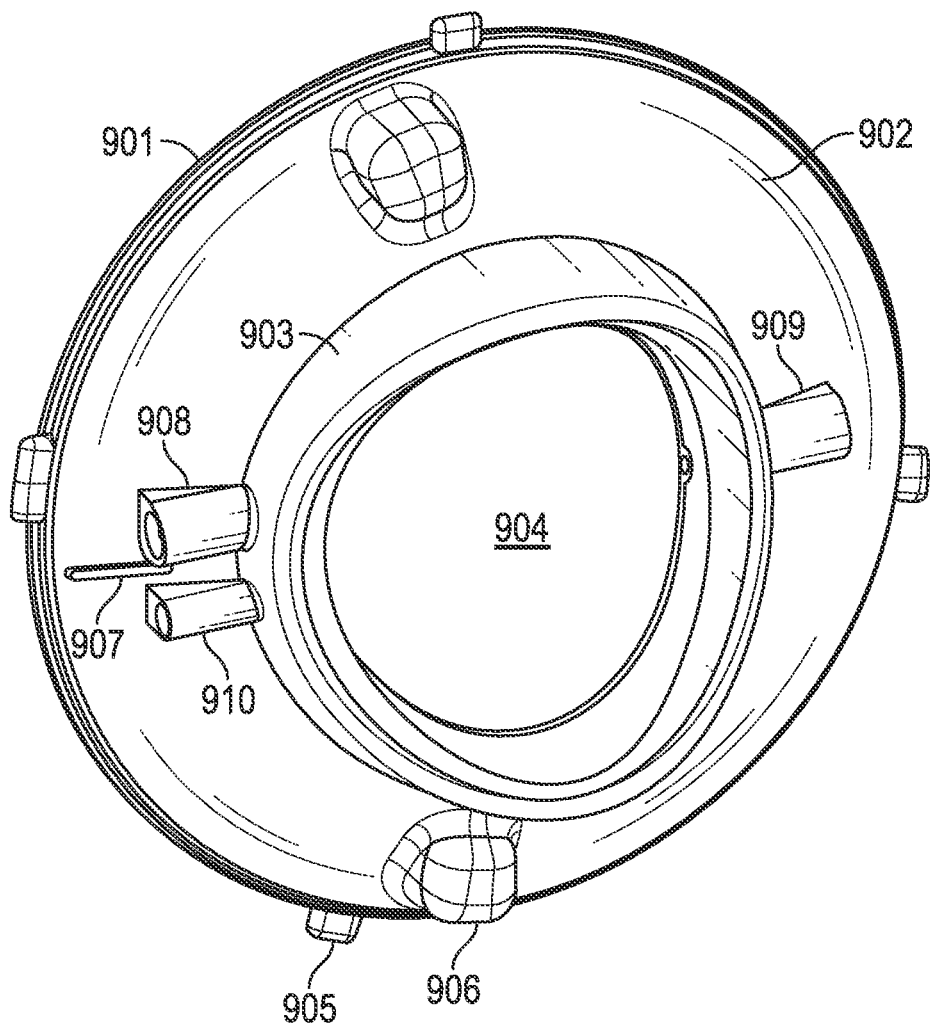
FIG. 9 is a schematic of an eye piece typically used on an ultra sound scanner.

FIG. 9 is a schematic of an eye piece typically used on an ultrasound scanner. FIG. 9 is an isometric view of an advanced eye piece for a precision scanning machine. Eye piece 901 is comprised of a plastic base 902 molded from a plastic such as ABS and a soft rubber conformable face seal 903 formed from a silicone thermo-plastic elastomer. The conformable face seal 903 is over-molded onto the plastic base 902 by a heat process typically applied to the conformable face seal 903. Plastic base 902 also includes attaching mechanisms 905 which attach the eye piece to the mounting ring (not shown) which is typically attached to the main scanner housing; thumb and finger protrusions 906 used to rotate the eye piece into the mounting ring; indexing ridge 907 which prevents over-rotation of the eye piece as it is rotated into the mounting ring attached to the main scanner housing; and fill port 908, vent port 910 and drain port 909. Ports 908, 909 and 910 allow fluid flow through the eye piece base 901.

The eye piece is attached and sealed to a mounting ring which is, in turn, attached to the main scanner body by a groove molded as part of the eye piece base 902 and a matching tongue formed as part of the mounting ring. The eye piece is rotated into position with the mounting ring where the tongue and groove form a contact connection which compresses and seals as the parts are rotated into position.

A sealed hygienic barrier membrane (not shown) is formed as part of the eye piece and is typically located, where the soft rubber face seal 903 is connected to the eye piece base 901. This membrane is typically attached onto the plastic eye piece base 902 by an adhesive backing commonly used in medical disposable components. The thickness of the membrane is designed for transmission of light (such as a fixation light, and transmission of acoustic energy emitted by the transducer and reflected by a component of the eye. The membrane is hermetically sealed to prevent saline solution from contaminating the distilled water in the machine body (saline solution or tap water inside the machine body can corrode plastic, ceramic and metal components) and to prevent the distilled water in the machine body from contaminating the saline solution in the eye piece. As disclosed in U.S. Pat. No. 8,758,252, eye piece membranes have been made from materials such as, for example, polyethylene, mylar, polypropylene; vinylidene chloride; polyvinylidene chloride; or DuraSeal (made by Diversified Biotech) which is polyethylene based material free of adhesives. A preferred material is medical grade polyethylene which has an acoustic impedance slightly higher than that of water (about 2.33 million kg/m2-s compared to 1.54 million kg/m2-s for water). The thickness of the membrane is preferably in the range of about 10 to about 30 microns. This thickness is a small part of an acoustic wavelength in water which is about 150 microns at 10 MHz and about 20 microns at 80 MHz.

The fill, drain and vent ports shown in FIG. 9 are designed and sized for fast fill (to minimize the patient's time with their eye immersed in the saline solution), for venting of any bubbles that may form, for example, if the seal on the patient's head leaks or the patient pulls away from the machine, and for rapid draining of the saline solution back into the plastic saline bag after scanning is completed. As can be appreciated, the fill and vent ports are on the top of the eye piece and the drain port is on the bottom of the eye piece.

Figure 10A:
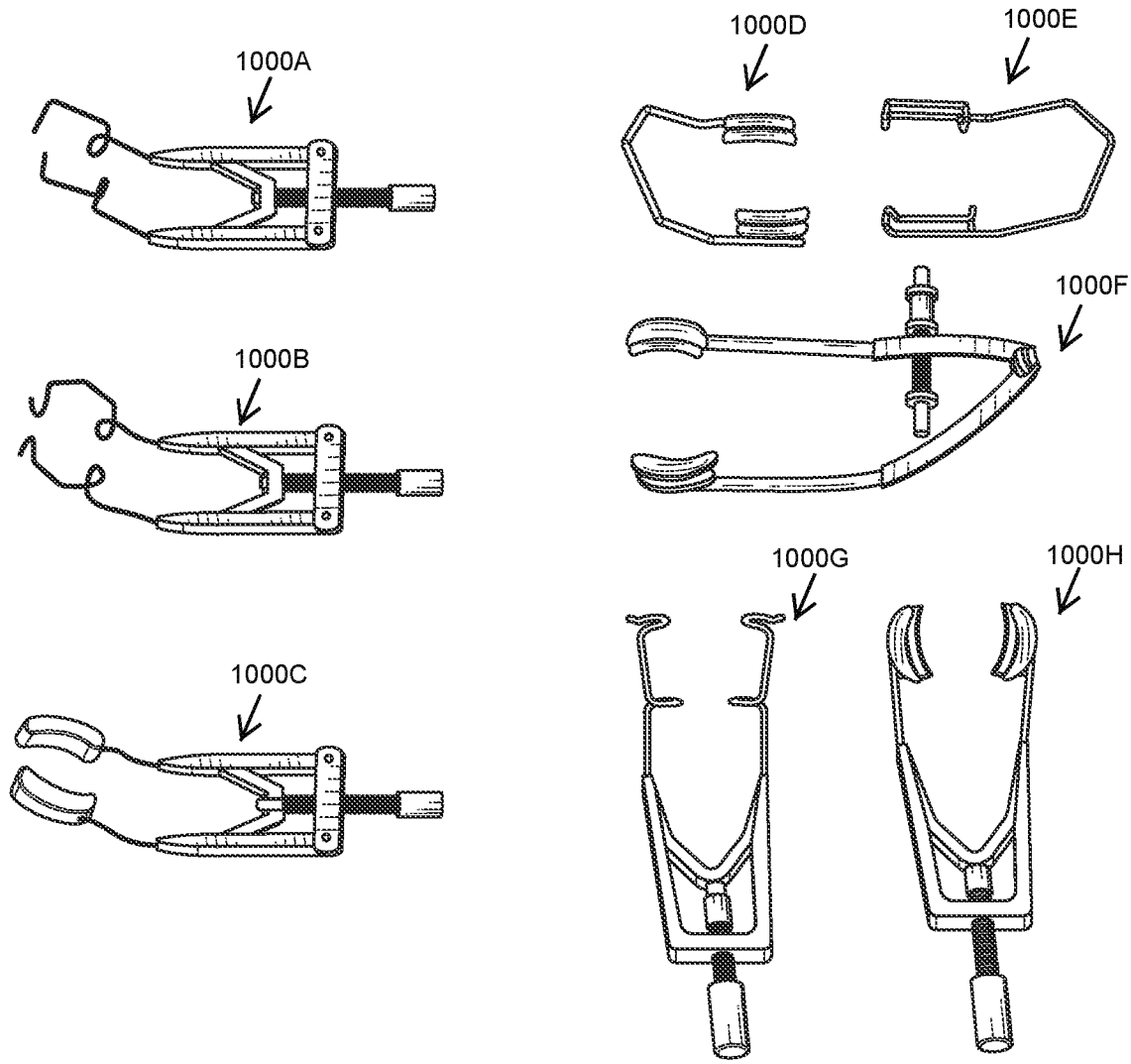
FIGS. 10A and 10B are examples of eye speculums.
Figure 10B:
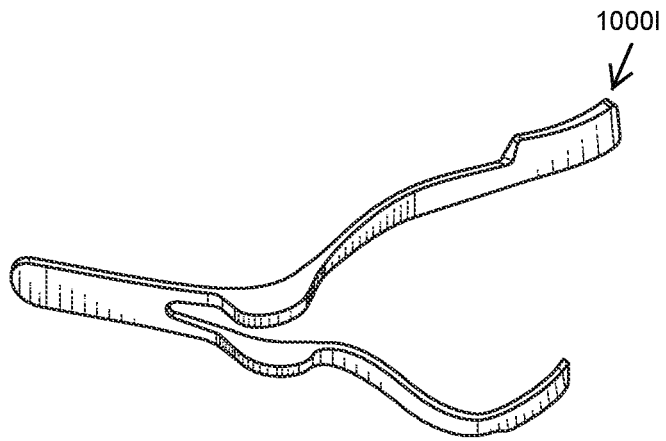

FIGS. 10A and 10B illustrate examples of eye speculums 1000A, 1000B, 1000C, 1000D, 1000E, 1000F, 1000G, 1000H, 1000I. FIG. 10a shows a number of types of eye speculums that have been used. None of these would be useful to hold open eyelids during imaging with the ultrasound scanner such as shown in FIG. 7. Adjustments of these speculums could not be made by the patient.

FIG. 10b shows a molded plastic speculum taken from U.S. D601,698. This speculum can be used to hold open eyelids during imaging with the ultrasound scanner such as shown in FIG. 7. This speculum causes some patient discomfort but cannot be adjusted by the instrument operator or patient once the patient is engaged with the eye piece of the scanning instrument shown in FIG. 7.

Figure 11:
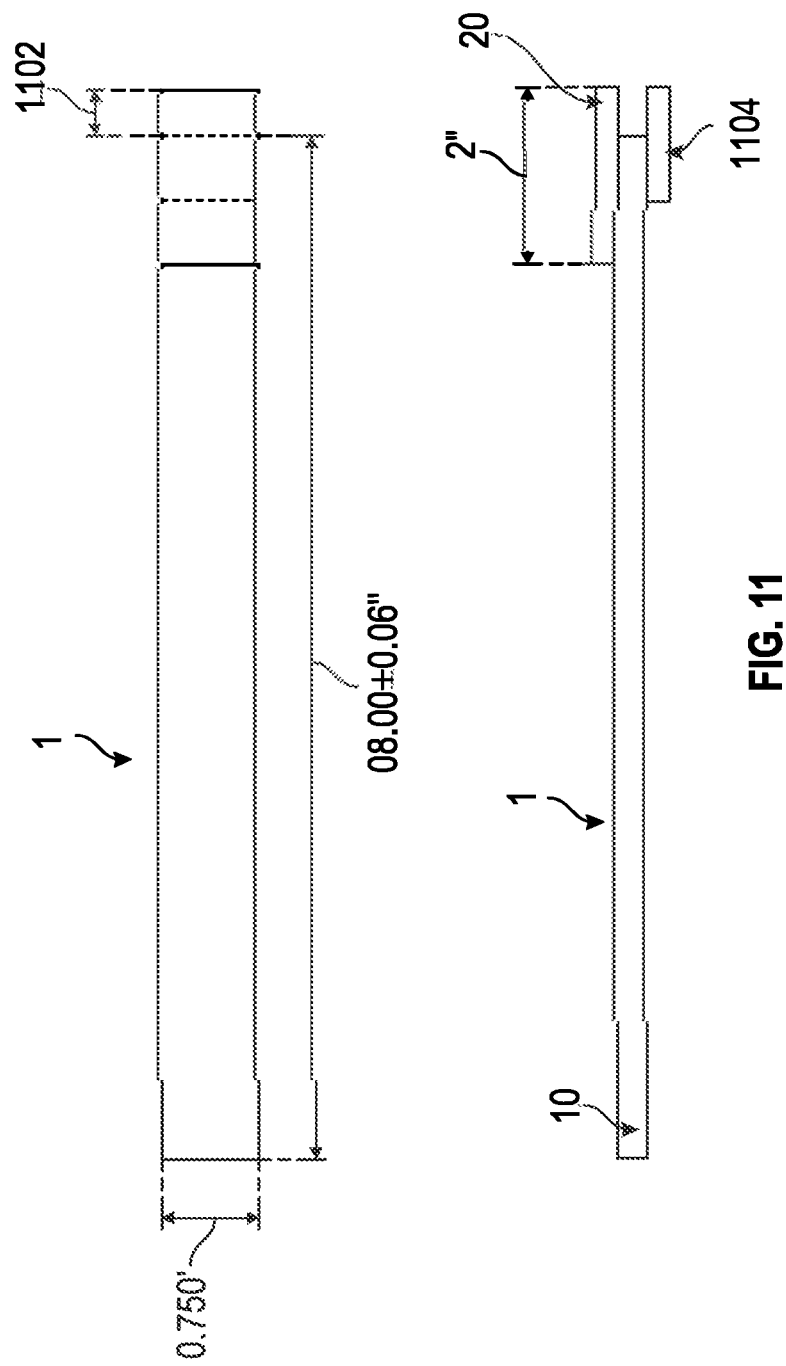
FIG. 11 is a drawing of an alternative eye strip of the present disclosure.

FIG. 11 shows a further view of an eye strip 1 having a base strip 10 and an adhesive strip 12. As shown, the eye strip and its components can have various dimensions. It will be appreciated that in some embodiments, the overhanging portion 1102 of the adhesive strip can be 0.300+/−0.100". In some embodiments, the overhanging portion is less than 0.5". In some embodiments, the overhanging portion is 0.25". The eye strip may include a release liner 1104. In addition, the base strip may be a material called polyester film sold under the trademark MELINEX® 329, the properties of which are described here: https://usa.dupontteijinfilms.com/wp-content/uploads/2017/01/329-Datasheet.pdf [retrieved Dec. 21, 2020], which is incorporated herein by reference.

A number of variations and modifications of the inventions can be used. As will be appreciated, it would be possible to provide for some features of the inventions without providing others.

The present disclosure, in various embodiments, includes components, methods, processes, systems and/or apparatus substantially as depicted and described herein, including various embodiments, sub-combinations, and subsets thereof. Those of skill in the art will understand how to make and use the present disclosure after understanding the present disclosure. The present disclosure, in various embodiments, includes providing devices and processes in the absence of items not depicted and/or described herein or in various embodiments hereof, including in the absence of such items as may have been used in previous devices or processes, for example for improving performance, achieving ease and\or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover though the description of the disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed:

1. An apparatus for controlling eyelid movement, comprising:
    a base strip extending between a first end and a second end of the base strip by a first length, wherein the base strip is made of a flexible but non-stretching material; and
    an adhesive strip extending between a first end and a second end of the adhesive strip by a second length, wherein at least one surface of the adhesive strip has an adhesion surface that is positioned on a surface of the base strip, and wherein a portion of the adhesive strip overhangs one of the first end or the second end of the base strip by a third distance that is between approximately 6.5% and 13.5% of the second distance.

2. The apparatus of claim 1, wherein the base strip has a lower Young's modulus than the adhesive strip.

3. The apparatus of claim 1, wherein the second length is between approximately 35% and 40% of the first length.

4. The apparatus of claim 1, wherein another surface of the at least one surface of the adhesive strip is an adhesion surface, and a liner is positioned on the adhesion surface oriented away from the base strip.

5. The apparatus of claim 1, wherein the base strip is a polyester film with a thickness between surfaces of between approximately 23 microns to 350 microns.

6. The apparatus of claim 1, wherein the adhesion surface of the adhesive strip comprises a pressure sensitive tackified acrylate adhesive.

7. The apparatus of claim 1, wherein the adhesive strip comprises a backing that is a transparent, perforated ethylene vinyl acetate.

8. The apparatus of claim 1, wherein the base strip and the adhesive strip are each approximately 0.75 inches wide.

9. The apparatus of claim 1, wherein the flexible but non-stretching material is polyester film.

10. A system for controlling eyelid movement, comprising:
    an eye diagnostic device having an eye piece with a top edge and a bottom edge, wherein the eyepiece is configured to receive a patient's eye in a space between the top edge and the bottom edge;
    a first eye strip having a first adhesive strip joined to a first base strip, wherein the first adhesive strip is shorter than the first base strip, wherein a portion of the first adhesive strip overhangs an end of the first base strip, wherein the overhanging portion of the first adhesive strip is configured to adhere to an upper eyelid of the patient's eye, and wherein the first eye strip presses into the top edge of the eyepiece with a first friction force to resist an eyelid closing force; and
    a second eye strip having a second adhesive strip joined to a second base strip, wherein the second adhesive strip is shorter than the second base strip, wherein a portion of the second adhesive strip overhangs an end of the second base strip, wherein the overhanging portion of the second adhesive strip is configured to adhere to a lower eyelid of the patient's eye, and wherein the second eye strip presses into the bottom edge of the eyepiece with a second friction force to resist the eyelid closing force.

11. The system of claim 10, wherein the first adhesive strip comprises an adhesion surface and an opposing non-adhesion surface, wherein the non-adhesion surface contacts the top edge of the eyepiece to produce the first friction force.

12. The system of claim 10, wherein the top edge and the bottom edge of the eyepiece are part of a rubber face seal that is joined to a rigid portion of the eyepiece.

13. The system of claim 12, wherein the rubber face seal is a silicone thermos-plastic elastomer.

14. The system of claim 10, wherein the overhanging portion of the first adhesive strip is between approximately 6.5% and 13.5% of an overall length of the first adhesive strip.

15. The system of claim 14, wherein the overall length of the first adhesive strip is between approximately 35% and 40% of an overall length of the first base strip.

16. The system of claim 11, wherein the adhesion surface of the first adhesive strip comprises a pressure sensitive tackified acrylate adhesive.

17. A method for controlling eyelid movement, comprising:
- providing a first eye strip having a first adhesive strip joined to a first base strip, wherein the first adhesive strip is shorter than the first base strip, and wherein a portion of the first adhesive strip overhangs an end of the first base strip;
- adhering the overhanging portion of the first adhesive strip to an upper eyelid of a patient;
- providing a second eye strip having a second adhesive strip joined to a second base strip, wherein the second adhesive strip is shorter than the second base strip, and wherein a portion of the second adhesive strip overhangs an end of the second base strip;
- adhering the overhanging portion of the second adhesive strip to a lower eyelid of the patient; and
- pressing the patient's face into an eyepiece of an eye diagnostic device such that a first friction force is created between the first eye strip and a top edge of the eyepiece and a second friction force is created between the second eye strip and a bottom edge of the eyepiece, wherein the first and second friction forces resist a closing force of the upper and lower eyelids of the patient.

18. The method of claim 17, further comprising:
- forming a watertight seal between the face of the patient with the first and second eye strips adhered to the upper and lower eyelids of the patient and the eyepiece.

19. The method of claim 18, further comprising:
- filling a space defined by the eyepiece with a fluid, wherein the eye diagnostic device is an ultrasound imaging device configured to transmit an ultrasound pulse through the fluid and into an eye of the patient.

20. The method of claim 18, further comprising:
- filling a space defined by the eyepiece with a fluid, wherein the eye diagnostic device is an optical imaging device configured to transmit an optical pulse through the fluid and into an eye of the patient.

21. The method of claim 17, further comprising:
- pulling a distal end of the first base strip to impose a force on the first eye strip that is at least greater than the first friction force to further open the eye of an patient.

22. The method of claim 17, wherein the overhanging portion of the first adhesive strip is between approximately 6.5% and 13.5% of an overall length of the first adhesive strip.

23. The method of claim 22, wherein the overall length of the first adhesive strip is between approximately 35% and 40% of an overall length of the first base strip.

* * * * *